(12) United States Patent
Koester et al.

(10) Patent No.: US 12,325,031 B2
(45) Date of Patent: Jun. 10, 2025

(54) GRAPHENE-BASED DIELECTROPHORESIS SENSOR AND METHOD

(71) Applicant: Regents of the University of Minnesota, Minneapolis, MN (US)

(72) Inventors: Steven John Koester, Edina, MN (US); Sang-Hyun Oh, Plymouth, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 684 days.

(21) Appl. No.: 16/972,858

(22) PCT Filed: Jun. 5, 2019

(86) PCT No.: PCT/US2019/035558
§ 371 (c)(1),
(2) Date: Dec. 7, 2020

(87) PCT Pub. No.: WO2019/236690
PCT Pub. Date: Dec. 12, 2019

(65) Prior Publication Data
US 2021/0245172 A1 Aug. 12, 2021

Related U.S. Application Data

(60) Provisional application No. 62/680,777, filed on Jun. 5, 2018.

(51) Int. Cl.
*B03C 5/00* (2006.01)
*G01N 27/447* (2006.01)
*G01N 33/487* (2006.01)

(52) U.S. Cl.
CPC ....... *B03C 5/005* (2013.01); *G01N 27/44756* (2013.01); *G01N 33/487* (2013.01); *B03C 2201/26* (2013.01)

(58) Field of Classification Search
CPC .. B03C 5/005; B03C 5/026; G01N 27/44756; G01N 33/4833
See application file for complete search history.

(56) References Cited

U.S. PATENT DOCUMENTS

| 4,647,362 | A | 3/1987 | Watanabe |
| 5,569,367 | A | 10/1996 | Betts et al. |

(Continued)

FOREIGN PATENT DOCUMENTS

| CN | 103531482 | 1/2014 |
| CN | 107462621 | 12/2017 |

(Continued)

OTHER PUBLICATIONS

Xie et al., "Development of a 3D Graphene Electrode Dielectrophoretic Device," Journal of Visualized Experiments, Jun. 2014, 88, e51696, 11 pages (Year: 2014).

(Continued)

*Primary Examiner* — C. Sun
(74) *Attorney, Agent, or Firm* — Fish & Richardson P.C.

(57) ABSTRACT

A dielectrophoretic (DEP) sensor includes a graphene electrode adjacent a channel for confining a target particle in a liquid, a surface probe attached to a surface of the graphene electrode, the surface probe having a selective reaction with the target particle, and a voltage source electrically connected to the graphene electrode and configured to apply a voltage to the graphene electrode to cause DEP trapping of the target particle at the graphene electrode.

14 Claims, 10 Drawing Sheets

(56) References Cited

U.S. PATENT DOCUMENTS

| | | | |
|---|---|---|---|
| 7,635,420 | B1 | 12/2009 | Li et al. |
| 10,888,875 | B2 | 1/2021 | Oh et al. |
| 2003/0146100 | A1* | 8/2003 | Huang ............... G01N 33/5438 |
| | | | 204/547 |
| 2003/0157587 | A1 | 8/2003 | Gomez et al. |
| 2006/0063183 | A1* | 3/2006 | Segawa .................. B03C 5/005 |
| | | | 435/287.2 |
| 2006/0201811 | A1 | 9/2006 | Hamers et al. |
| 2007/0246364 | A1 | 10/2007 | Amlani et al. |
| 2011/0108422 | A1 | 5/2011 | Heller et al. |
| 2011/0192726 | A1 | 8/2011 | Chen et al. |
| 2012/0037919 | A1 | 2/2012 | Xu et al. |
| 2012/0103813 | A1* | 5/2012 | Sato ........................ B03C 5/026 |
| | | | 204/547 |
| 2012/0134880 | A1* | 5/2012 | Kurkina ............... G01N 33/487 |
| | | | 977/773 |
| 2013/0248368 | A1 | 9/2013 | Kim et al. |
| 2014/0216935 | A1 | 8/2014 | Vezenov |
| 2014/0291606 | A1 | 10/2014 | Avouris et al. |
| 2015/0107999 | A1 | 4/2015 | Weber et al. |
| 2015/0218630 | A1 | 8/2015 | Sun et al. |
| 2017/0028408 | A1 | 2/2017 | Menachery et al. |
| 2017/0292934 | A1* | 10/2017 | Azpiroz ........... G01N 27/44791 |
| 2017/0368557 | A1 | 12/2017 | Chi et al. |
| 2018/0361400 | A1 | 12/2018 | Oh et al. |
| 2021/0220840 | A1 | 7/2021 | Oh et al. |

FOREIGN PATENT DOCUMENTS

| | | |
|---|---|---|
| EP | 2434278 | 3/2012 |
| JP | 2006-084301 | 3/2006 |
| JP | 2007-006858 | 1/2007 |
| JP | 2012-065649 | 4/2012 |
| JP | 2012-247189 | 12/2012 |
| JP | 2013-224947 | 10/2013 |
| JP | 2016-180652 | 10/2016 |
| JP | 2018-009993 | 1/2018 |
| JP | 2018-021827 | 2/2018 |
| JP | 2018-036154 | 3/2018 |
| KR | 20180033711 | 4/2018 |
| KR | 101900049 | 9/2018 |
| KR | 20200074785 | 6/2020 |
| KR | 102134394 | 7/2020 |

OTHER PUBLICATIONS

Pumera et al., "Graphene in biosensing," Mater. Today, Jul. 6, 2011, 14(7-8):308-315.

Suvarnaphaet et al., "Graphene-Based Materials for Biosensors: A Review," Sensors, Sep. 21, 2017, 17(10):2161, 24 pages.

Ameri et al., "Utilization of graphene electrode in transparent microwell arrays for high throughput cell trapping and lysis," Biosensors Bioelectronics., 61:625-630, 2014.

Barik et al., "Dielectrophoresis-Enhanced Plasmonic Sensing with Gold Nanohole Arrays," Nano Lett., 14:2006-2012, 2014.

Barik et al., "Graphene-edge dielectrophoretic tweezers for trapping of biomolecules," Nat. Communications, 8:1867, Nov. 2017, 9 pages.

Barik et al., "Ultralow-Power Electronic Trapping of Nanoparticles with Sub-10 nm Gold Nanogap Electrodes," Nano Lett., 16:6317-6324, 2016.

Bonaccorso et al., "Graphene photonics and optoelectronics," Nature Photonics., 4:611-622, Sep. 2010.

Chen et al., "Label-Free Detection of DNA Hybridization using Transistors Based on CVD Grown Graphene," Biosensors Bioelectronics, 41:103-109, Mar. 2013.

Chou et al., "Electrodeless Dielectrophoresis of Single- and Double-Stranded DNA," Biophys. Journal, 83(4):2170-2179, Oct. 2002.

Cinti et al., "Electrochemical Biosensors for Rapid Detection of Foodborne *Salmonella*: A Critical Overview," Sensors, 17(8):1910, Aug. 2017, 22 pages.

Deen et al., "Graphene-Based Quantum Capacitance Wireless Vapor Sensors," IEEE Sensors Journal, 14(5):1459-1466, Dec. 2013.

Dong et al., "Electrical Detection of DNA Hybridization with Single-Base Specificity Using Transistors Based on CVD-Grown Graphene Sheets," Adv. Mater., 22(14):1649-1653, Apr. 2010.

Ebrish et al., "Operation of multi-finger graphene quantum capacitance varactors using planarized local bottom gate electrodes," Appl. Phys. Letters, 100:143102, Apr. 2012, 4 pages.

Electroschematics.com [online], "Varactors," Sep. 28, 2009, retrieved on Mar. 19, 2020, retrieved from URL<https://www.electroschematics.com/varactors/>, 2 pages.

EP Extended Search Report in EP Appln. No. 19816011.1, dated Jun. 22, 2021, 8 pages.

Fowler et al., Practical Chemical Sensors from Chemically Derived Graphene, ACS Nano., 3(2):301-306, 2009.

Freedman et al., "Nanopore sensing at ultra-low concentrations using single-molecule dielectrophoretic trapping," Nat Commun., 7:10217, 2016, 9 pages.

Gascoyne et al., "Dielectrophoresis-Based Sample Handling in General-Purpose Programmable Diagnostic Instruments," Proc. IEEE Inst. Electr. Electron Eng., 92(1):22-42, Jan. 2004.

Geiselmann et al., "Three-dimensional optical manipulation of a single electron spin," Nat Nanotechnology., 8:175-179, Mar. 2013.

Giuliodori et al., "Development of a graphene oxide-based assay for the sequence-specific detection of double-stranded DNA molecules," PLoS One, 12(8):e0183952, Aug. 2017, 17 pages.

Grigorenko et al., "Graphene plasmonics," Nature Photonics., 6:749-758, Nov. 2012.

Guo et al., "Development of a Novel Quantum Dots and Graphene Oxide Based FRET Assay for Rapid Detection of invA Gene of *Salmonella*," Front. Microbiol., 8:8, Jan. 2017, 7 pages.

Jose et al., "Individual Template-Stripped Conductive Gold Pyramids for Tip-Enhanced Dielectrophoresis," ACS Photonics., 1:464-470, 2014.

Kakatkar et al., "Detection of DNA and Poly-l-lysine using CVD Graphene-Channel FET Biosensors," Nanotechnology, 26(12):125502, Mar. 2015, 5 pages.

Kim et al., "Multitarget Dielectrophoresis Activated Cell Sorter," Anal. Chem., 80(22):8656-8661, Nov. 2008.

Kurkina et al., "Label-free electrical biosensing based on electrochemically functionalized carbon nanostructures," Dissertation for the degree of Doctor Rerum Naturalium, Institut fur Anorganische und Analytische Chemie der Justus-Liebig-Universitat Giessen, Feb. 2012, 106 pages.

Kuzyk., "Dielectrophoresis at the nanoscale," Electrophoresis., 32:2307-2313, 2011.

Lee et al., "Optical separation of mechanical strain from charge doping in graphene," Nat. Commun., 3:1024, Aug. 2012, 8 pages.

Li et al., "Graphene-templated supported lipid bilayer nanochannels," Nano Lett., 16:5022-5026, 2016.

Li et al., "Large-Area Synthesis of High-Quality and Uniform Graphene Films on Copper Foils," Science, 324(5932):1312-1314, Jun. 2009.

Liu et al., "Biological and chemical sensors based on graphene materials," Chem. Soc. Rev., 41(6):2283-2307, Mar. 2012.

Loan et al., "Hall Effect Biosensors with Ultraclean Graphene Film for Improved Sensitivity of Label-Free DNA Detection," Biosensors Bioelectronics, 99:85-91, Jan. 2018.

Low and Avouris., "Graphene Plasmonics for Terahertz to Mid-Infrared Applications," ACS Nano., 8(2):1086-1101, 2014.

Low et al., "Polaritons in layered two-dimensional materials," Nature Mater., 16:182-194, Feb. 2017.

Lukacs et al., "Size-dependent DNA Mobility in Cytoplasm and Nucleus," J Biol Chem., 275(3):1625-1629, Jan. 21, 2000.

Ma et al., "Acetone Sensing Using Graphene Quantum Capacitance Varactors," 2016 IEEE Sensors Conference, Orlando, Florida, USA, Oct. 30-Nov. 3, 2016, 3 pages.

Neto et al., "The electronic properties of graphene," Rev Mod Phys., 81:109-162, Jan.-Mar. 2009.

Novoselov et al., "Electric Field Effect in Atomically Thin Carbon Films," Science, 306(5696):666-669, Oct. 2004.

Park et al., "Development of multiplex PCR assay for simultaneous detection of *Salmonella* genus, *Salmonella* subspecies I, Salm.

(56) References Cited

OTHER PUBLICATIONS

Enteritidis, Salm. Heidelberg and Salm. Typhimurium," J. Appl. Microbiol., 118(1):152-160, Jan. 2015.

PCT International Preliminary Report on Patentability in International Appln. No. PCT/US2019/035558, dated Dec. 8, 2020, 6 pages.

PCT International Search Report and Written Opinion in International Appln. No. PCT/US2019/035558, dated Sep. 10, 2019, 8 pages.

Pelton., "Modified spontaneous emission in nanophotonic structures," Nature Photonics., 9:427-435, Jul. 2015.

Ping et al., "Scalable Production of High-Sensitivity, Label-Free DNA Biosensors Based on Back-Gated Graphene Field Effect Transistors," ACS Nano, 10(9):8700-8704, Aug. 2016.

Regtmeier et al., "Dielectrophoretic Trapping and Polarizability of DNA: The Role of Spatial Conformation," Anal Chem., 82(17):7141-7149, Sep. 1, 2010.

Rodrigo et al., "Mid-infrared plasmonic biosensing with graphene," Science., 349(6244):165-168, Jul. 10, 2015.

Sanghavi et al., "Electrokinetic Preconcentration and Detection of Neuropeptides at Patterned Graphene-Modified Electrodes in a Nanochannel," Anal. Chemistry, 86(9):4120-4125, May 2014.

Schneider et al., "Tailoring the hydrophobicity of graphene for its use as nanopores for DNA translocation," Nat Commun., 4:2619, 2013, 7 pages.

Sheehan, and L. J. Whitman, "Detection Limits for Nanoscale Biosensors," Nano Lett., 5(4):803-807, Apr. 2005.

Squires et al., "Making it stick: convection, reaction and diffusion in surface-based biosensors," Nature Biotechnology., 26(4):417-426, Apr. 2008.

UMN.edu [online], "Researchers develop graphene nano 'tweezers' that can grab individual biomolecules," Dec. 4, 2017, retrieved on Jul. 7, 2021, retrieved from URL<https://cse.umn.edu/college/news/researchers-develop-graphene-nano-tweezers-can-grab-individual-biomolecules>, 3 pages.

WHO.int [online], "Food safety," available on or before Nov. 21, 2014 via Internet Archive: Wayback Machine URL<https://web.archive.org/web/20141121212113/http://www.who.int/mediacentre/factsheets/fs399/en/>, retrieved on Jul. 7, 2021, retrieved from URL<https://www.who.int/en/news-room/fact-sheets/detail/food-safety>, 6 pages.

Xu et al., "Electrophoretic and Field-Effect Graphene for All-Electrical DNA Array Technology," Nat. Commun., 5:4866, Sep. 2014, 9 pages.

Xu et al., "Nucleic Acid Biosensor Synthesis of an All-in-One Universal Blocking Linker Recombinase Polymerase Amplification with a Peptide Nucleic Acid-Based Lateral Flow Device for Ultrasensitive Detection of Food Pathogens," Anal. Chem., 90(1):708-715, Dec. 2017.

Yan et al., "Damping pathways of mid-infrared plasmons in graphene nanostructures," Nature Photonics., 7:394-399, May 2013.

Zhang et al., "Capacitive sensing of glucose in electrolytes using graphene quantum capacitance varactors," ACS Appl. Mater. Interfaces, 9(44):38863-38869, Oct. 2017.

Zhang et al., "Glucose sensing with graphene varactors," 2016 IEEE Sensors Conference, Orlando, Florida, USA, Oct. 30-Nov. 3, 2016, 3 pages.

Zheng et al., "Manipulating Nanoparticles in Solution with Electrically Contacted Nanotubes Using Dielectrophoresis," Langmuir, 20(20):8612-8619, Sep. 28, 2004.

U.S. Appl. No. 16/010,980, filed Jun. 18, 2018, Sang-Hyun Oh.

U.S. Appl. No. 17/121,285, filed Dec. 14, 2020, Sang-Hyun Oh.

Suehiro et al., "Selective detection of bacteria using dielectrophoretic impedance measurement method combined with antigen-antibody reaction," Conference Record of the 2001 IEEE Industry Applications Conference, 36th IAS Annual Meeting, Chicago, IL, Sep. 30-Oct. 4, 2001, 3:1950-1955.

* cited by examiner

GRAPHENE-BASED DIELECTROPHORESIS SENSOR AND METHOD

CROSS-REFERENCE TO RELATED APPLICATIONS

This application is a National Stage application under 35 U.S.C. § 371 of International Application No. PCT/US2019/035558, having an International Filing Date of Jun. 5, 2019, which claims priority to U.S. Application Ser. No. 62/680,777, filed on Jun. 5, 2018. The disclosure of the prior application is considered part of the disclosure of this application, and is incorporated in its entirety into this application.

BACKGROUND

According to the World Health Organization, 550 million people become ill from foodborne enteric diseases, and 230,000 people die from them each year. Infections from Salmonella spp. and Escherichia coli (E. coli) rank among the most common of these enteric diseases. Salmonella spp. is a bacterium found in animals that, if ingested, can cause serious health problems. Such problems are particularly serious in people with high risk for complications such as young children, older adults and people with weakened immune systems. Similarly, E. coli is a coliform bacterium that can cause sickness or even death in humans, depending on the strain of the bacteria and the susceptibility of the person. In Minnesota and across the country, Salmonella spp. and E. coli outbreaks continue to be an ongoing threat to public health.

Commonly used test methods for pathogen bacterial DNA involve culture and/or polymerase chain reaction (PCR) analysis, which is a laboratory technique used to amplify a target DNA molecule using a series of repeated amplification sequences. PCR has excellent sensitivity, but requires dozens of cycles to determine the presence or absence of a particular species, is both time-consuming and costly, and often requires an initial enrichment culture step. Increasingly rapid and sensitive methods to detect pathogenic organisms in food products or clinical samples are being developed. In particular, methods to detect Salmonella spp. rapidly have been pursued because of the importance of this bacteria as a foodborne pathogen, recent advances have further improved the speed and sensitivity of detection using other methods, but these techniques still fall short of the speed and sensitivity required for hand-held systems.

A particularly promising method of DNA detection of hand-held systems involves the use of graphene-based sensors, and numerous reports in the literature have shown that graphene can provide an excellent alternative method to selectively sense DNA. Graphene is a two-dimensional sheet of $sp^2$-bonded carbon, which can be realized in monolayer form either through mechanical exfoliation, or through growth on copper using chemical vapor deposition (CVD).

Due to its monolayer nature, graphene can provide excellent sensitivity to adsorbed biomolecules, and can also be functionalized to provide selectively to chemically-active targets.

Conventional graphene sensors utilize simple diffusion processes to attract particles to the surface. This can be slow. On the other hand, dielectrophoresis (DEP) can be used to attract particles to a region of high electric field gradient, but does not provide a convenient means of selective sensing. In this invention, a sensor is described that solves the problem of how to achieve selectivity within a DEP-based sensors by the use of graphene which is functionalized with a probe material on the surface. It also provides a way to separate the DEP-attraction bias voltages, which are relatively large, and the sensing bias voltages, which are often smaller.

SUMMARY

In certain aspects, the invention features a graphene-edge dielectrophoretic (DEP) sensor that utilizes surface functionalization to achieve specificity and selective sensing. In some aspects, the invention features a methodology by which to detect the selective response of the sensor.

In some embodiments, the graphene-based DEP sensor utilizes surface functionalization on the graphene or adjacent surfaces (or substrates) to achieve selectivity. The graphene-based DEP sensor can use a time-varying excitation for DEP attraction that enables the sensor response to be read out independent of the DEP AC excitation.

Among other advantages, embodiments can achieve selectivity to a range of target molecules or biological particles using a DEP-based graphene sensor. Embodiments can also enable reading out the sensor response in the presence of a relatively large AC excitation meant to attract particles to the graphene edge.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1a shows the sensor with the attached probe on the graphene surface, in a solution containing the target. FIG. 1b shows the sensor with the targets attracted to the graphene edges using DEP via an applied AC bias. FIG. 1c shows the targets bonding to nearby probes after the DEP excitation is removed, enabling sensor readout.

FIG. 2a shows the sensor with the attached probe on the graphene surface, in a solution containing the target. FIG. 2b shows the sensor with the targets attracted to the graphene edges using DEP via an applied AC bias. FIG. 2c shows the targets bonding to nearby probes after the DEP excitation is removed, enabling sensor readout.

FIGS. 6a-6e illustrate a graphene-edge DEP tweezer fabrication process.

Like reference symbols in the various drawings indicate like elements.

DETAILED DESCRIPTION

Figure 1A:
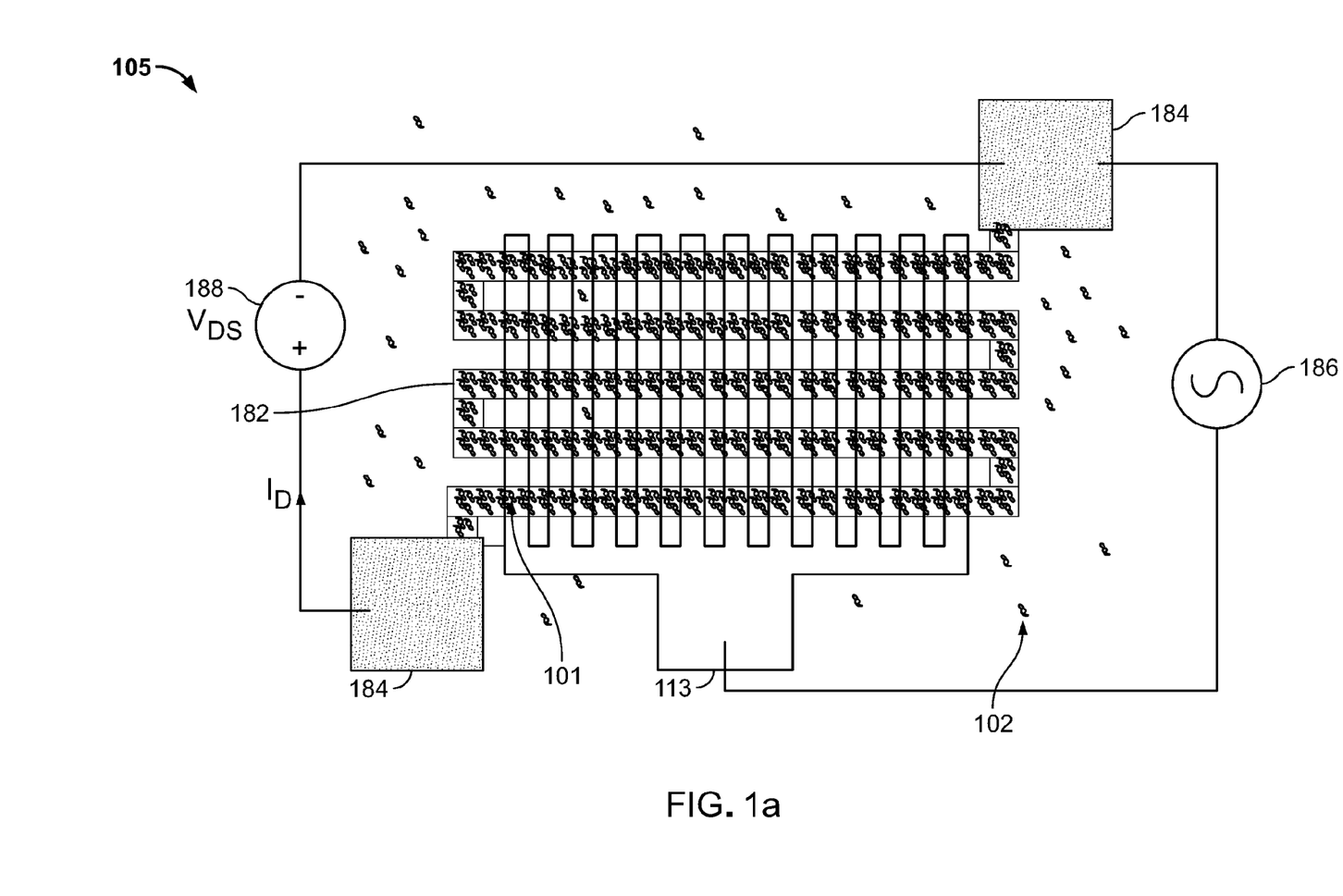
FIGS. 1a-1c are schematic diagrams showing a top view of a resistance-based DEP sensor.

FIG. 1a shows an embodiment of a graphene-edge dielectrophoretic sensor 105. The particular sensor operates in the resistive sensing mode as we have described previously in Provisional Application No. 62/521,096, entitled "Electrodes formed from 2D materials for dielectrophoresis and systems and methods for utilizing the same," filed on Jun. 16, 2017, and in U.S. 2018/0361400, filed Jun. 18, 2018, the entire contents both of which are hereby incorporated by reference.

DEP sensor 105 includes the first fingered electrode 113, a graphene electrode 182, and contacts 184. The contacts 184 are electrically coupled to the graphene electrode 182. The DEP sensor 105 is a three-terminal device, in which the first fingered electrode 113 serves as a gate electrode, and the two contacts 184 serves as the source and drain terminals. The graphene electrode 182 is arranged in a serpentine shape to increase crossing sites with the first fingered electrode 113. Increasing the crossing sites leads to increased number of edges where particles can be trapped. For example, widths of the serpentine strips of the graphene electrode 180 can range from 100 nm to 5 µm, and widths of the fingers of the first fingered electrode 113 can range from 0.1 µm to 5 µm.

The graphene electrode 182 is electrically isolated from the first fingered electrode 113. For example, an insulating layer similar to the insulating layer 130 may be arranged between the first fingered electrode 113 and the graphene electrode 182. As such, an example stack-up of the DEP sensor 105 may include, in the order as listed, the first fingered electrode 113, the insulating layer, and the graphene electrode 182. The insulating layer may act as the "gate oxide" of the 3 terminal FET device formed by the graphene electrode 182 and the first fingered electrode 113.

The contacts 184 may be formed from various conductive materials. Examples of conductive materials include metals, silicides, or alloys, such as Gold, Palladium, Platinum, Tungsten, Chromium, Titanium, Iridium, Molybdenum, Aluminum, or Copper. In some implementations, different layers of conductive materials can be stacked to form the contacts 184.

The DEP sensor 105 can be electrically measured by applying a DC voltage, an AC voltage, or both (collectively referred to as "measurement voltage") between the two ends of the graphene electrode 182 through the contacts 184, and measuring the resulting drain current (ID) while applying an AC voltage ("trapping voltage") between the first fingered electrode 113 ("gate electrode") and the graphene electrode 182 to induce DEP trapping. The trapping voltage can be applied through a voltage source 186 and the measurement voltage can be applied through a source meter 188 configured to apply a voltage and measure corresponding current. Initially, a trapping voltage is applied between the gate electrode 113 and the graphene electrode 182 at a frequency that does not correspond to DEP trapping (e.g., 1 MHz) for a particular type of particles, and no particles are trapped.

The measurement voltage is typically smaller than the trapping voltage to mitigate a voltage drop across the two terminals of the graphene electrode 182 caused by the flow of the drain current ID. For example, the measurement voltage can be 10 to 100 times smaller than the amplitude of the trapping voltage.

In some implementations, the trapping voltage can have a DC bias in addition to the AC voltage. The DC bias can be used, for example, to bias the graphene electrode 182 to control its conductivity.

As shown in FIG. 1a, a surface probe 101 is attached to the graphene electrode 182, where the probe is designed to have a selective reaction with a target 102. The probe and target can feature of any complementary pair of molecules, proteins, aptamers, antibodies, lipids, vesicles, cell-derived particles, functionalized nanoparticles or whole cells that have the property that the probe can be attached to the surface of the graphene, and that that the target is a polarizable particle such that it can be attracted to the graphene surface using DEP and can selectively attach to the surface probe on the graphene.

An example of such a probe/target pair is single-stranded DNA molecules with complementary matching. Another example is functionalization of graphene using biotin or biotin-labeled proteins for the detection of streptavidin targets.

Selective attachment of the target to the probe can be detected using the sensor. This can be achieved using either the capacitive or resistive sensing means described previously in Provisional Application No. 62/521,096 and U.S. 2018/0361400 using a graphene-edge DEP geometry. The sensing can be achieved using an "attract-and-listen" mode, where the target particles are first attracted to the graphene surface using a DEP excitation, and then the excitation is turned off and the graphene sensor response is evaluated using a smaller signal.

Figure 1B:
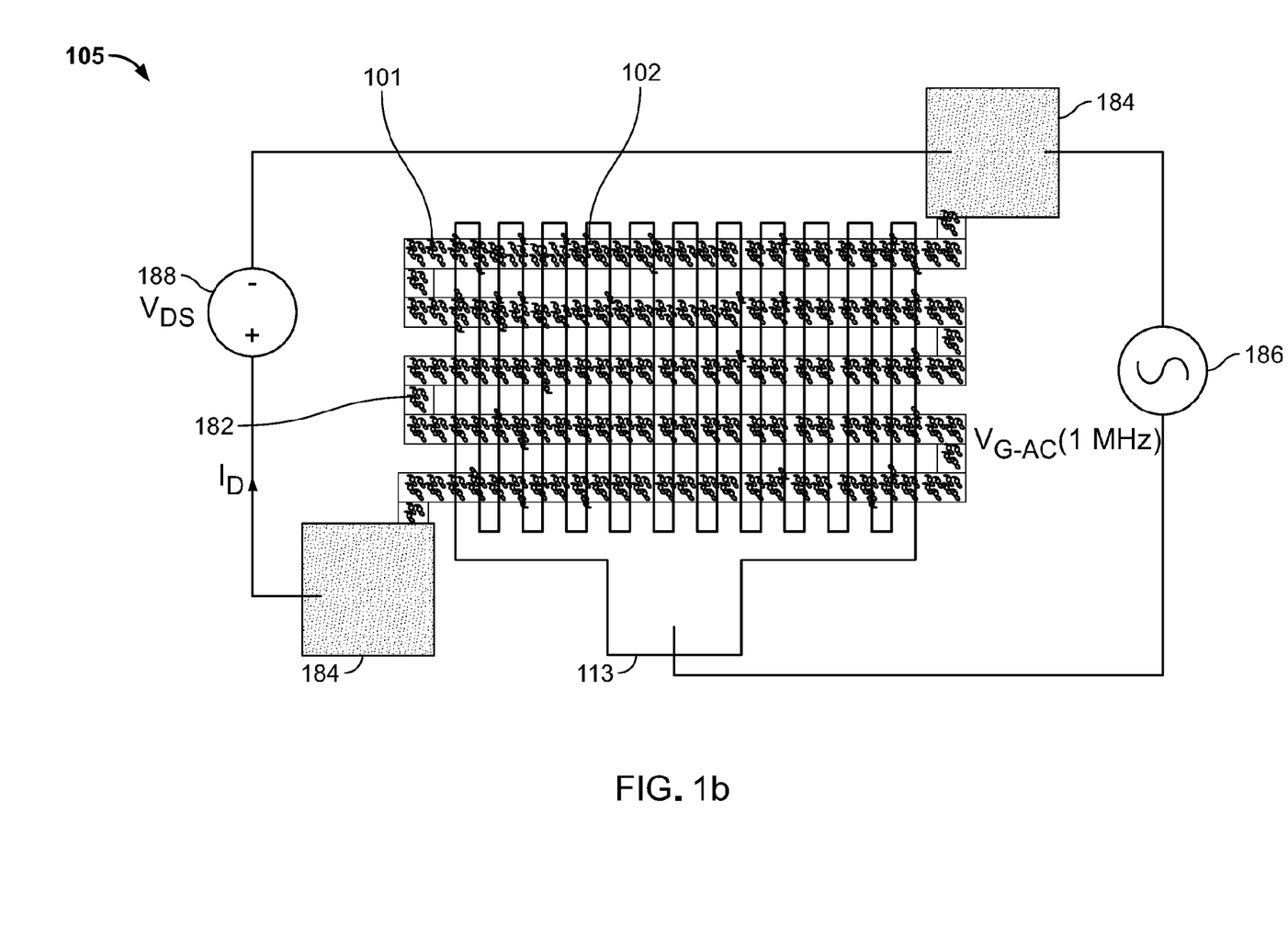
Figure 1C:
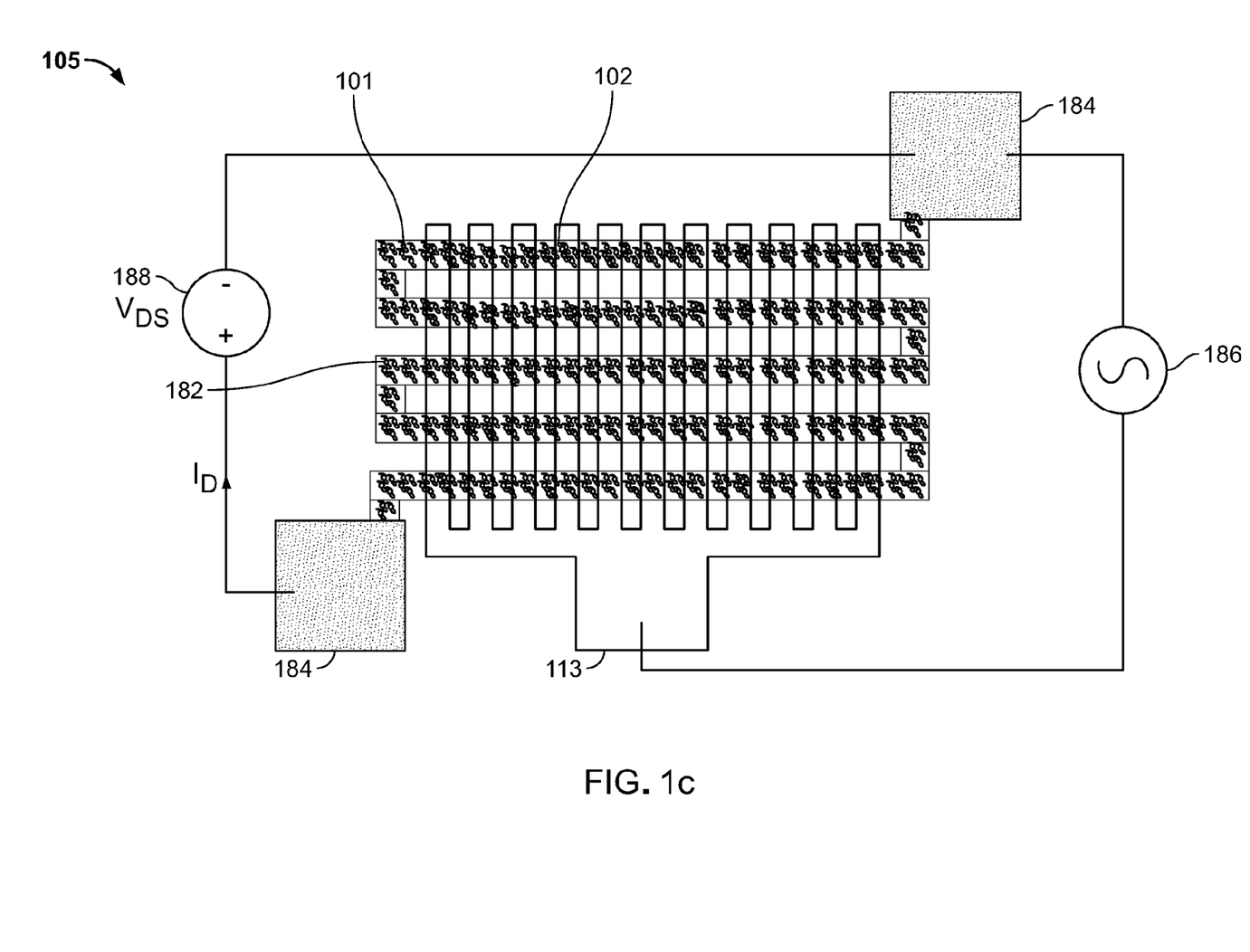

A diagram of this mode is illustrated in FIGS. 1a-1c which show DNA detection, where prior to the DEP attraction pulse, the target DNA is attracted to the regions of the graphene where the edges cross a gate edge. After release of the DEP pulse, as shown in FIG. 1c, the target DNA can attach to the probe DNA on the graphene surface nearby thus creating an electrical response. This response can be achieved using the resistive configuration shown in FIGS. 1a-1c or in a capacitive configuration as illustrated in FIGS. 2a-2c.

Figure 2A:
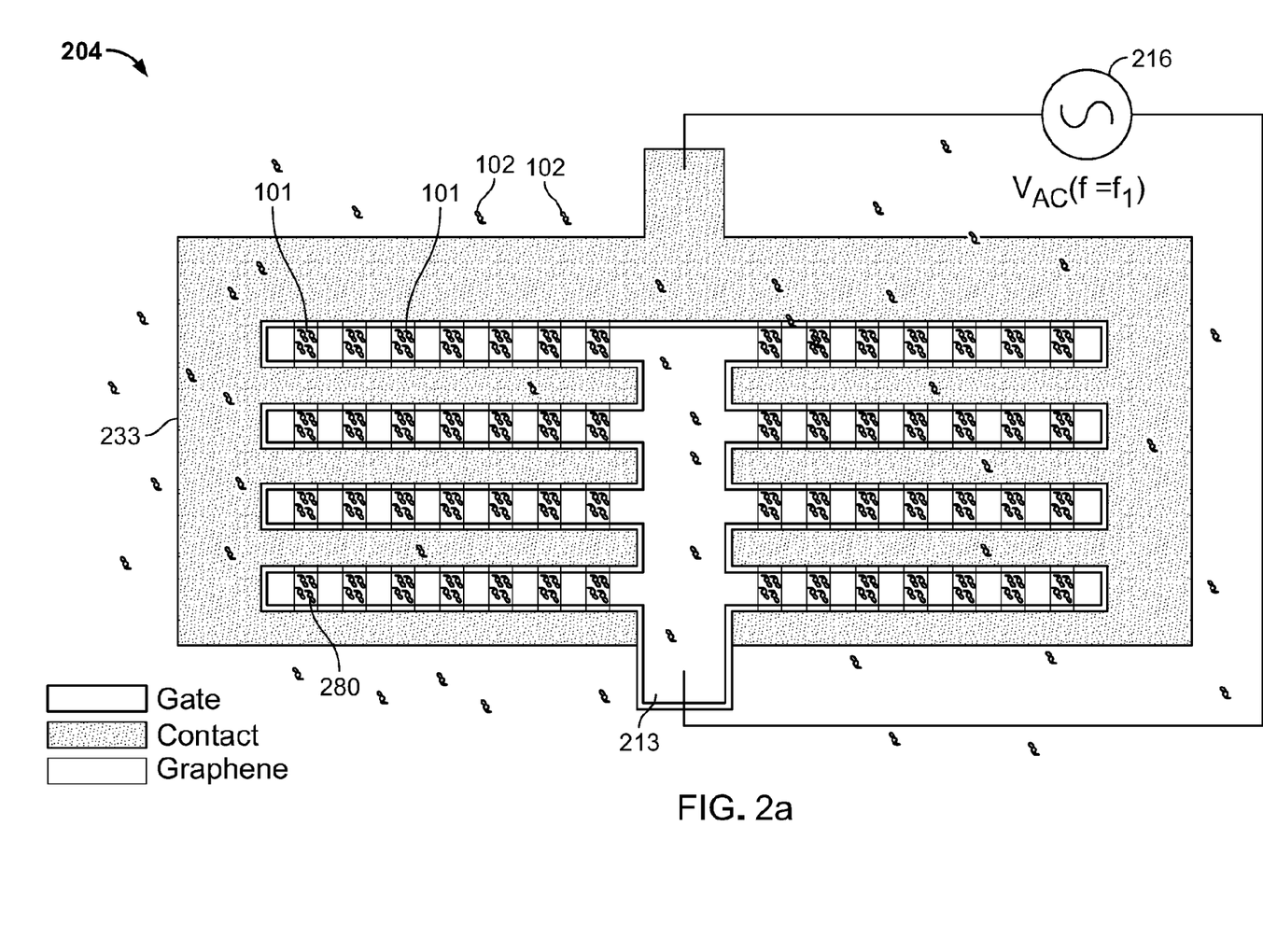
FIGS. 2a-2c are schematic diagrams showing a top view of a capacitance-based DEP sensor.
Figure 2B:
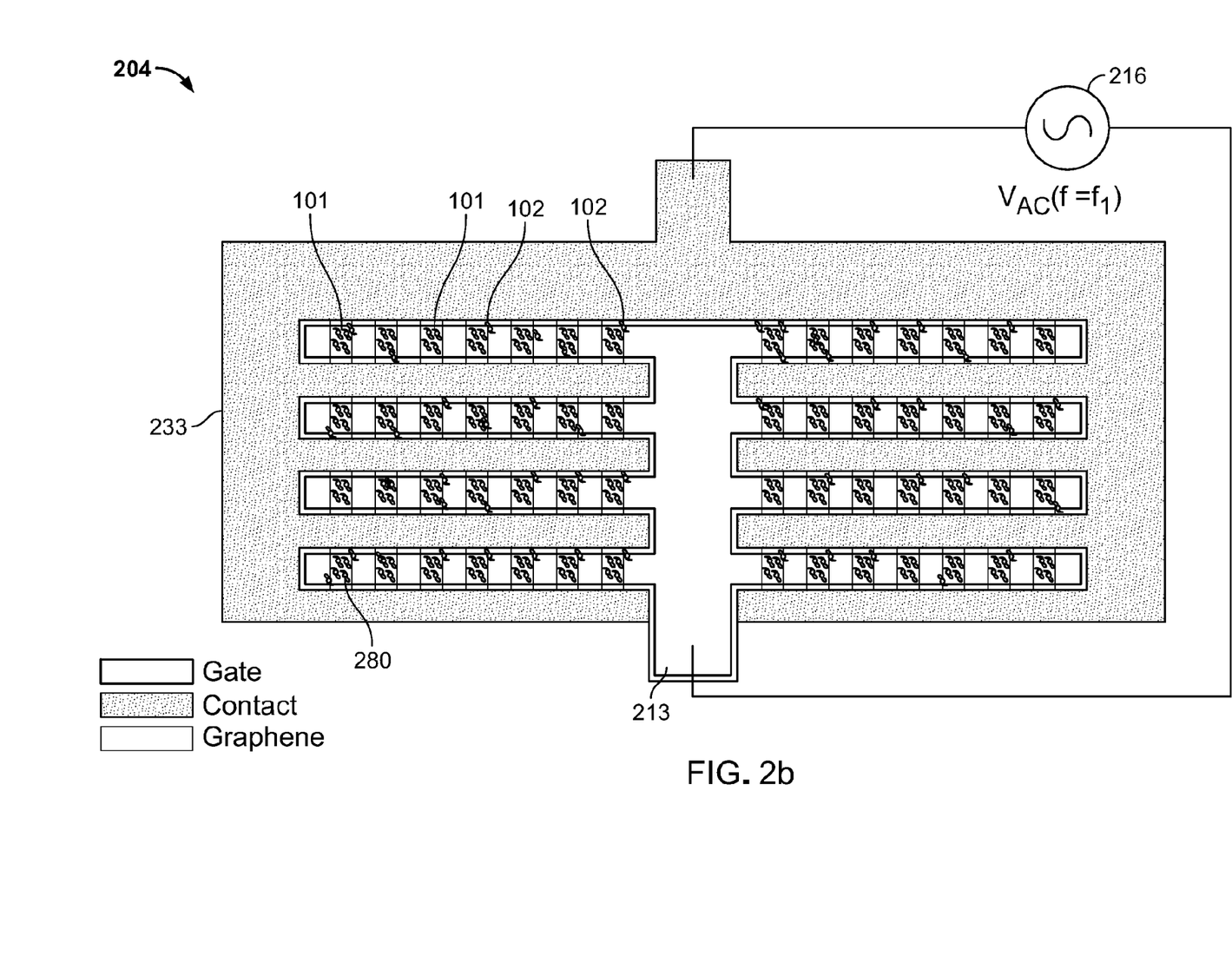
Figure 2C:
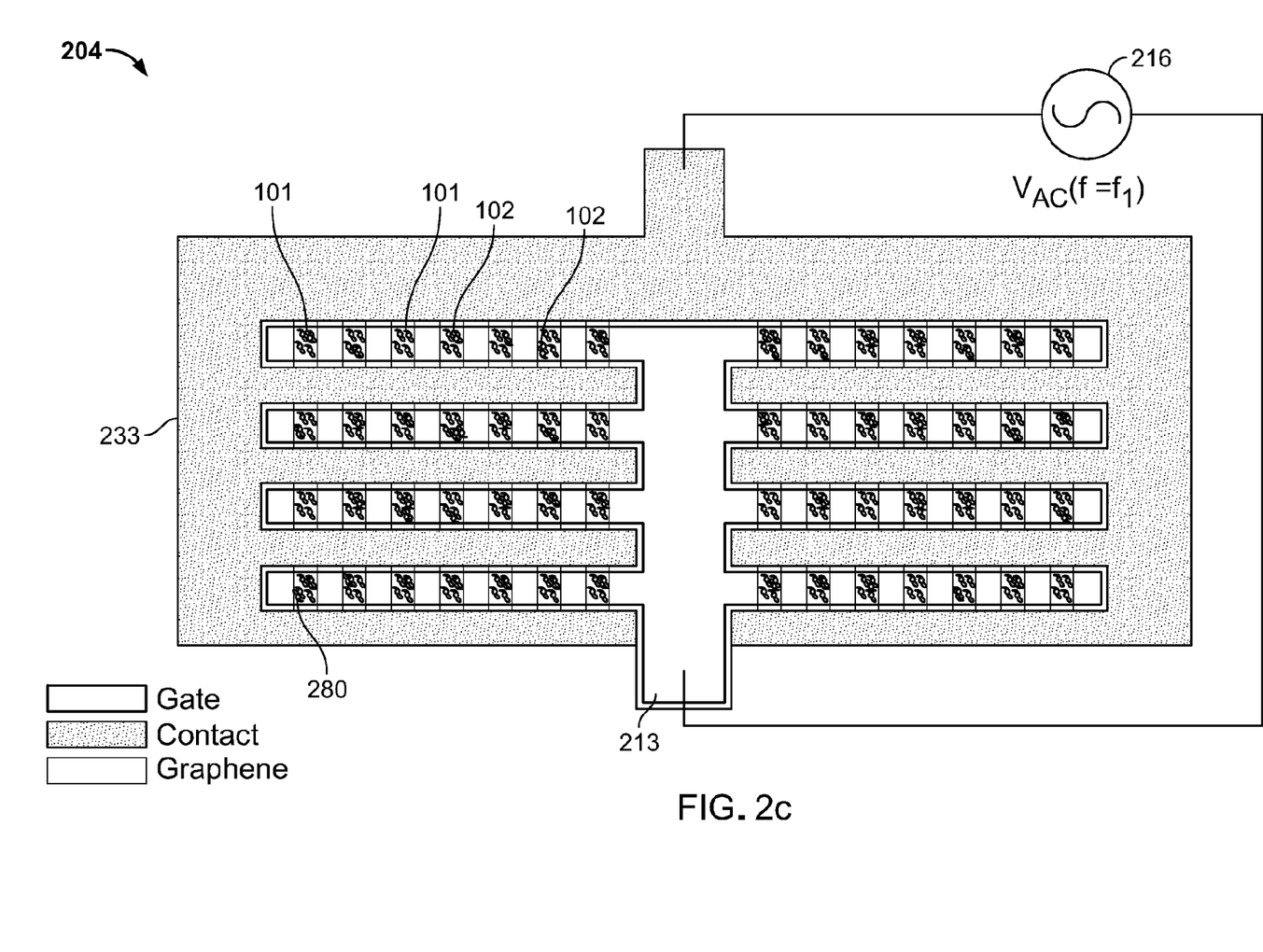

FIG. 2F shows a top view of a graphene varactor-integrated DEP device 204. The DEP device 204 includes a first fingered electrode 213, a second fingered electrode 233, and a graphene electrode 280. The graphene electrode 280 is electrically coupled to the second fingered electrode 233. The graphene electrode 280 has been subdivided into several smaller fingers to increase the number of edges and crossings of the graphene electrode 280 over the first finger electrode 213, where particles can be trapped. For example, the width of the subdivided fingers can range from 100 nm to 5 µm.

The graphene electrode 280 is electrically isolated from the first fingered electrode 213. For example, an insulating layer similar to the insulating layer 130 may be arranged between the first fingered electrode 213 and the graphene electrode 280. As such, an example stack-up of the DEP device 204 may include, in the order as listed, the first fingered electrode 213, the insulating layer, the graphene electrode 280, and the second fingered electrode 233. Further, other layers of materials may be present between the first fingered electrode 213, the insulating layer, and the graphene electrode 280.

The first and second fingered electrodes 213 and 233 may be formed from various conductive materials. Examples of conductive materials include metals, silicides, or alloys, such as Gold, Palladium, Platinum, Tungsten, Chromium, Titanium, Iridium, Molybdenum, Aluminum, or Copper. In some implementations, different layers of conductive materials can be stacked to form the first and second electrodes 213 and 233. Such stacking may be beneficial for improving adhesion between the metal and the insulating layer or the graphene, and for improving the quality of electrical contact to the graphene electrode 280.

Initially, an AC bias is applied between a the first fingered electrode 213 ("gate electrode") and the second fingered electrode 233 coupled to the graphene electrode 280 at a frequency that does not correspond to DEP trapping (e.g., 1 MHz) for a particular type of particles, and no particles are trapped as a result. The AC bias can be applied through a voltage source 216.

Figure 3:
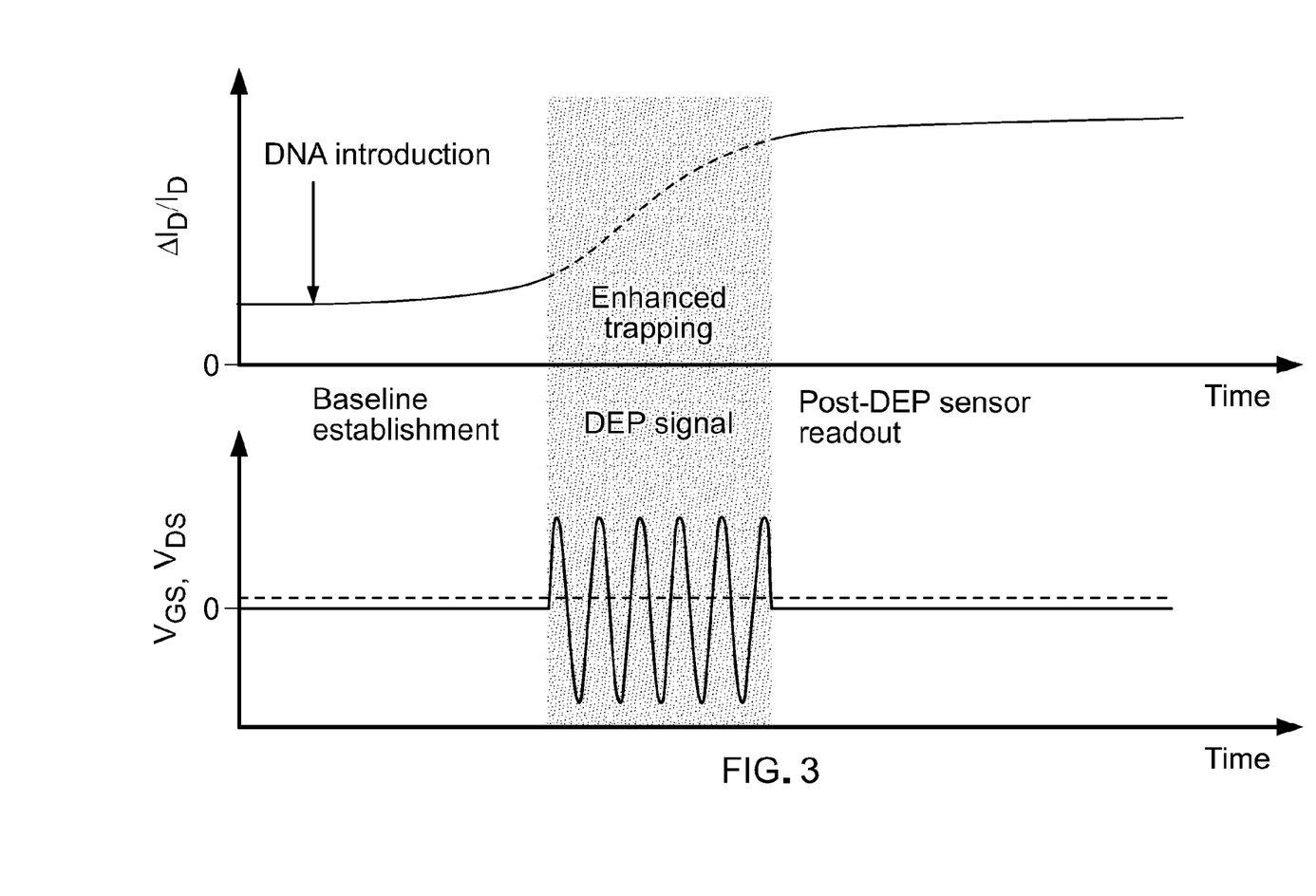
FIG. 3 shows plots of the applied voltage signal and anticipated response for a resistance-based DEP sensor.

The voltages applied (lower plot) and the anticipated response (upper plot) are shown in FIG. 3 for the resistive sensing mode. Here, the current can be readout in this device by applying a DC drain-to-source voltage, $V_{DS}$, and a constant gate voltage $V_{GS}$. When the DNA is applied to the sample, the response is typically slow. However, if a larger amplitude AC $V_{GS}$ signal is applied, DEP allows attraction of the DNA to the sample edges, accelerating the device response. Once the AC signal is removed the sensor reads a change in current, associated with trapping the target molecules to the surface. This readout could also be achieved by sweeping the gate voltage and monitoring the current to determine the gate voltage, the Dirac voltage, at which a minimum current occurs.

Figure 4:
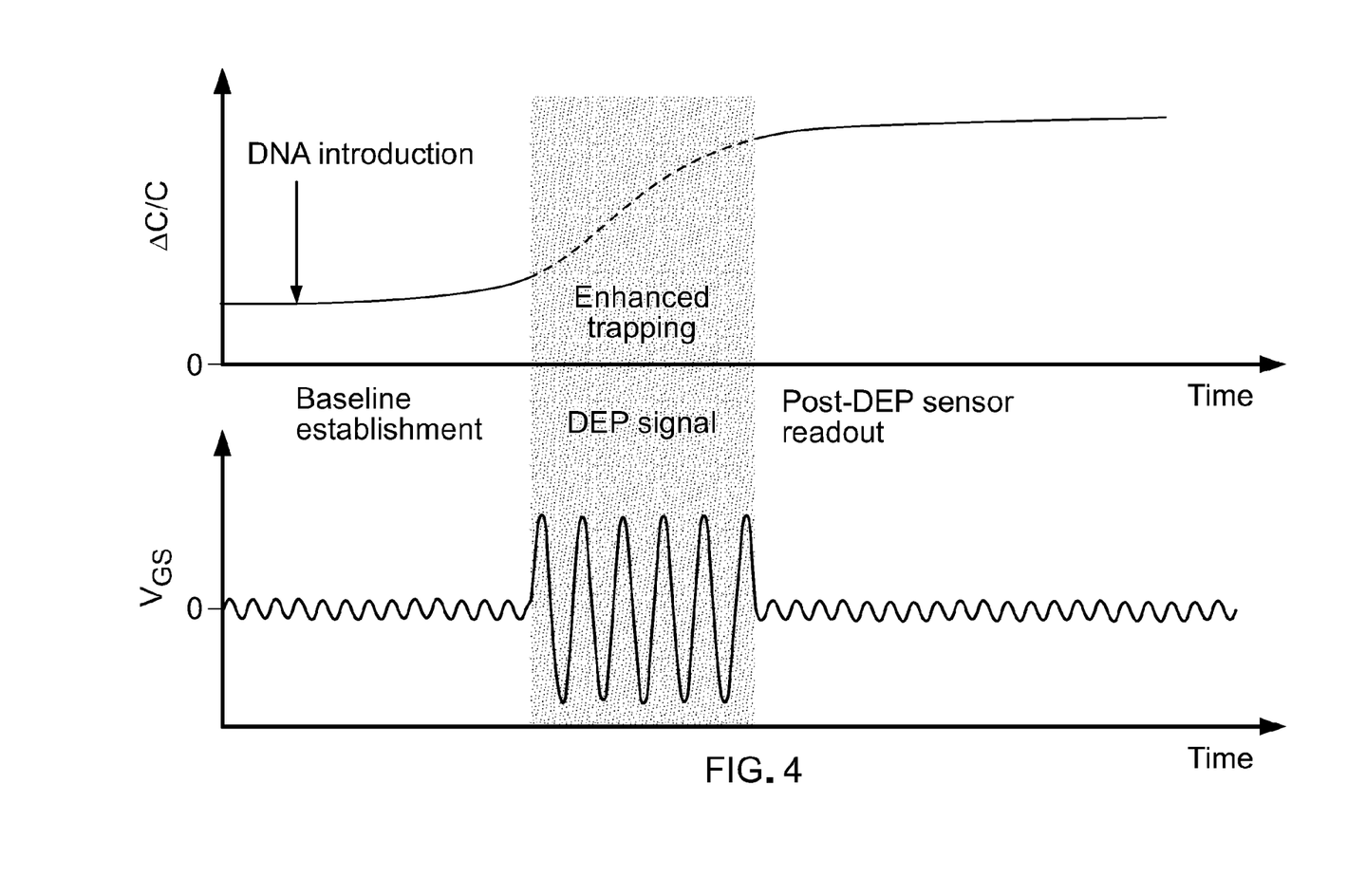
FIG. 4 shows plots of the applied voltage signal and anticipated response for a capacitance-based DEP sensor.

In FIG. 4, a sensing scenario for a capacitive-based sensor is shown. Here, the sensor is read out in a simple two-terminal configuration using a small AC gate bias. Once again, to accelerate the device response, a larger AC bias can be applied and then reduced again to read out the sensor capacitance response. Similar to the resistive sensor, the readout could also be achieved by sweeping the gate voltage and monitoring the Dirac voltage, which is the gate voltage at which the capacitance is minimum.

Figure 5:
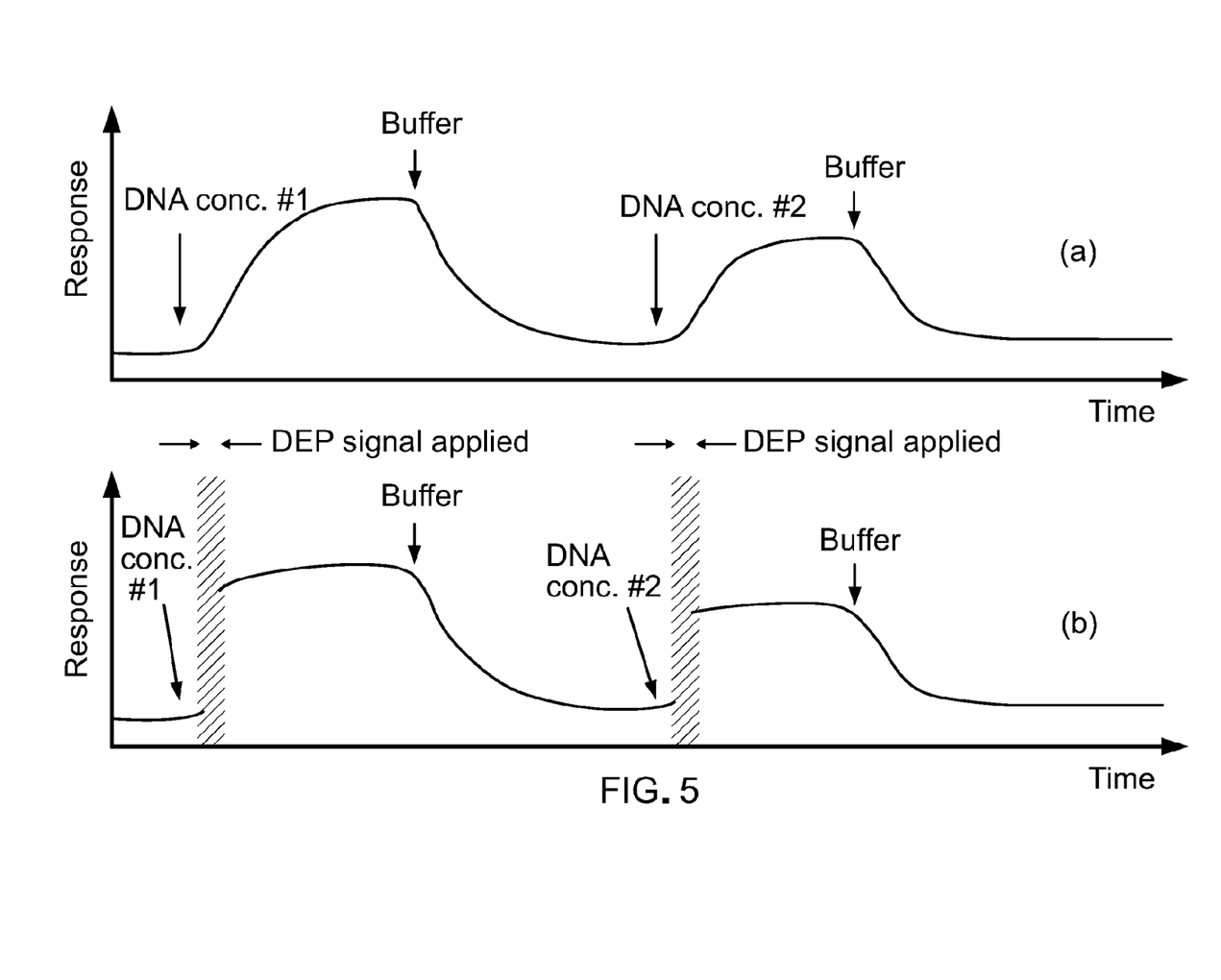
FIGS. 5a and 5b show plots of an anticipated response of a capacitance-based DEP sensor with varied AC bias.

As shown in FIG. 5, in some embodiments, this scenario is repeated and utilized for different concentrations of the target analyte, with the benefit of speeding the response compared to allowing the analytes to move to the surface through simple diffusive processes. This also differs from an alternative mode of sensing, where the DEP signal is applied continuously and the sensor response is read out concurrently with the DEP signal. A similar pulse sequence could be utilized to perform negative DEP, where unwanted particles are repelled from the surface after the sensor is exposed to the target-containing fluid. The sensing modality would be similar, except the frequency of the excitation would be such that certain particles in solution would be repelled.

In general, the sensors and techniques disclosed above can be implemented in a variety of applications. For example, they can be deployed in point of care sensors. In some embodiments, the embodiments are deployed in DNA-based bar-code sensors.

Prophetic Example 1: Fabrication and Trapping Verification of Sensors

DEP-based sensors are fabricated and their trapping capability validated as follows. The existing graphene variable capacitor (or "varactor") fabrication process (see, e.g., M. A. Ebrish, H. Shao, and S. J. Koester, "Operation of multi-finger graphene quantum capacitance varactors using planarized local bottom gate electrodes," Appl. Phys. Lett. 100, 143102 (2012).) is modified to make it suitable for trapping large densities of particles near the graphene surface.

Figure 6A:
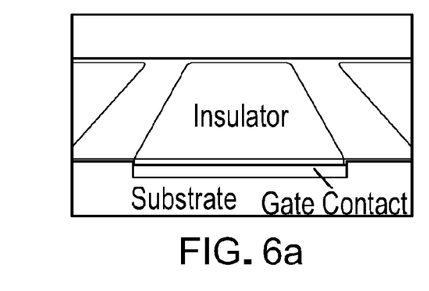
FIG. 6a shows gate oxide recess and gate metal patterning.
Figure 6B:
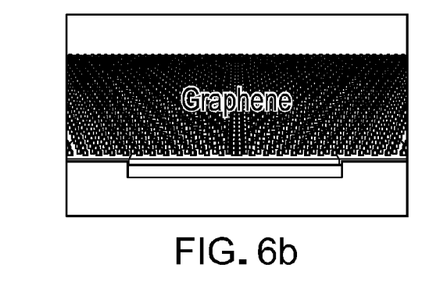
FIG. 6b shows graphene transfer.

An example fabrication process for the graphene-edge DEP sensors is shown in FIGS. 6a-6e. The device fabrication starts with a silicon wafer upon which thick $SiO_2$ is grown by thermal oxidation. Next, a gate contact electrode is patterned using optical lithography and the oxide recessed to a depth of ~50 nm and then gate metal (usually Ti/Pd) is deposited and lifted off to form a quasi-planar electrode (FIG. 6a). After the gate metallization, thin $HfO_2$ is deposited (usually ~7-10 nm) on the entire sample using atomic-layer deposition (ALD). Next, chemical vapor deposited (CVD) graphene is transferred onto the sample using a PMMA handle layer, where the PMMA is subsequently removed using a solvent clean and vacuum annealing (FIG. 6b).

Figure 6C:
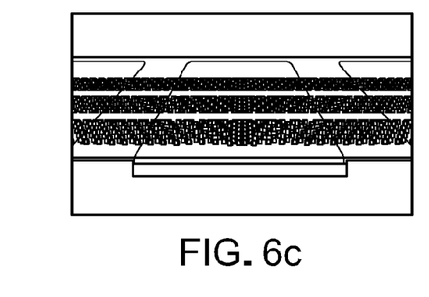
FIG. 6c shows graphene patterning into trapping segments.
Figure 6D:
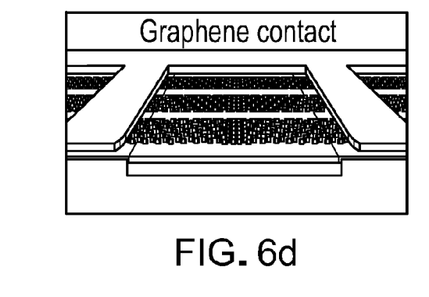
FIG. 6d shows contact metallization and lift off.
Figure 6E:
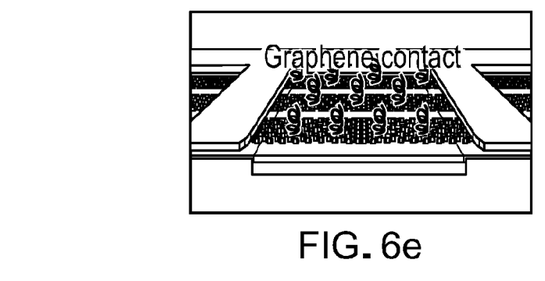
FIG. 6e shows the surface functionalization with a probe object.

Next, the graphene is patterned into a series of narrow strips, creating a greater number of edges where molecules can be trapped. Using optical lithography, the strips are as small as 2 μm wide with 4 μm pitch. Using electron-beam lithography, the strips are as narrow as 100 nm with 200 nm pitch. A schematic of the patterned graphene is shown in FIG. 6c. Next, Cr/Au (10/100 nm) metallization is patterned to form Ohmic contacts to the graphene as shown in FIG. 6d. The device fabrication can also include a thick (several micron) isolation layer such as SU-8 which is patterned and opened only above the active device area to form a micro-volume for fluid confinement during testing. Finally, functionalization is applied to attach probes to the graphene surface, as shown in FIG. 6e.

Different device geometries can be explored to determine an optimal structure to realize simultaneous trapping and sensing. There are several factors in this design optimization. These can include: (1) the number of edges necessary in order to achieve sufficiently effective trapping; (2) capacitance or resistive sensing; and (3) the optimal sequence of excitations to attract and sense the DNA fragments.

The sensor can be tested using filtered DNA samples in 1 mM KCl buffer (see, e.g., A. Barik, Y. Zhang, R. Grassi, B. P. Nadappuram, J. B. Edel, T. Low, S. J. Koester, and S.-H. Oh, "Graphene-edge dielectrophoretic tweezers for trapping of biomolecules," Nat. Commun. 8, 1867 (2017).), however more complex media with additional particles such as cell membranes and protein residue can be investigated. For food-borne pathogen detection, the DNA samples could include fragments of *Salmonella typhimurium*. The fragments vary in length from 1 kb to 100 bp based upon the type of PCR method (gel-based, cybergreen, or real-time) used to obtain the samples.

Prophetic Example 2: DNA Probe Attachment to Graphene and Selective DNA Sensing for *Salmonella typhimurium* and *E. coli* Using Graphene-Edge DEP Tweezers This example demonstrates two main elements: (1) surface functionalization of probe DNA on graphene and (2) sensing verification using the device structure shown in FIG. 6(d).

1-pyrenebutyric acid N-hydroxysuccinimide ester (PBASE) is attached to the graphene surface. The pyrene end of the PBASE attaches to the graphene through π-π interactions, while the succinimide portion extends outward from the graphene enabling bonding to the probe DNA. In order to attach the probe, the 5' end of the DNA is modified to include an amine group. This modified DNA is exposed to the PBASE-covered graphene in solution, and allowed to crosslink with the succinimide to form a stable functionalization layer. In general, the functionalization procedure is achieved by soaking the entire substrate in a probe-DNA-containing solution such as acetonitrile, though this process can readily be modified to achieve locally functionalized devices on the same chip using nozzle-based or 3D printing, thus enabling multiplexed sensing capability.

The attachment of the probe DNA to the graphene surface can first be verified on blanket graphene layers using atomic force microscopy (AFM) and Raman spectroscopy. Functionalization molecules on graphene can be verified using Raman spectroscopy, both by identifying peaks specific to the functionalization species as well as analyzing shifts in the G and 2D peaks that demonstrate systematic changes in the electron or hole concentration in the graphene. After functionalization has been verified using these techniques, the DNA probes are attached to graphene on a sensor device structure. In these structures, the probe DNA attachment is further verified by analyzing the shift in the Dirac voltage. It is believed that Dirac point shifts are a reliable indicator of surface functionalization attachment as has been demonstrated using pyrene boronic acid functionalization (see, e.g., Reference Y. Zhang, R. Ma, X. Zhen, Y C. Kudva, P. Bühlmann, and S. J. Koester, "Capacitive sensing of glucose in electrolytes using graphene quantum capacitance varactors," ACS Appl. Mater. Interfaces 9, 38863-38869 (2017)). Here, the graphene functionalization can be verified using increasing concentrations of the probe-DNA containing solutions and the Dirac point shift monitored as a function of concentration. This verification is important, since residues from device processing could be present and comparison of the equivalent doping results from the bare graphene via Raman and the device graphene from electrical tests provide an important validation for subsequent sensing.

DEP-enhanced sensing of the graphene devices is verified as follows. Medium-to-high conductivity KCl solution are utilized with concentration roughly 0.1× of standard phosphate buffered saline (PBS). In the initial tests, 100-1000 bp DNA fragments extracted from *E. coli* and *Salmonella typhimurium* PCR are evaluated at concentrations ranging from 1 nM down to 1 fM. The probe DNA consists of single-stranded DNA and the target DNA consists of single-stranded DNA with complementary base pair matching to the probe.

The samples are tested using a flow cell geometry. In the testing procedure, a solution containing the target DNA is cycled over the exposed region of the prefunctionalized sensor. The flow-cell geometry allows a single device to be tested at varying DNA concentrations.

Parasitic effects caused by the conductivity of the buffer solution are minimized due to the SU-8 layer that isolates the extrinsic region of the sensor and only allows the active sensor region to interact with the test solution. However, if such issues persist, additional dilution of the sensing solution should be possible. A test chip that allows testing of the devices using a standard probe station is used, where the probes are located far from the active device region in the test liquid. In addition, all of the sensing experiments utilize differential sensing, where a "blank" sensor (functionalized with pyrene only) is utilized as the control device. By subtracting signals from the electrode without receptors, background signals, drift issues, and temperature variations can be rejected. Such differential sensing may be important in DEP where heating effects are possible due to the fluid motion induced by the AC excitation.

Two main sensing protocols are described, based upon the two types of sensors geometries shown in FIGS. 1a-1c and 2a-2c. The first is the resistance-based geometry shown in FIGS. 1a-1c. In this geometry, the graphene is patterned in a shape where the graphene crosses a multi-finger buried electrode several times. The graphene can be arranged in a serpentine geometry to increase the number of gate edge crossings within a specific area. In this geometry, a small DC or AC bias (on the order of 100 mV) is applied between the ends of the graphene serpentine. The sensor response is determined by monitoring the relative drain current change ($\Delta I_D/I_D$) at fixed values of Vis vs. time for various DNA concentrations. The sensing can be monitored without DEP, by simply setting the gate voltage, $V_{GS}$, to a fixed value and monitoring $\Delta I_D/I_D$ vs. time. This response time is set the baseline with which to compare the DEP-enhanced sensing and is limited by the diffusion time and subsequent hybridization of the target DNA at the sensor surface.

After this baseline is established, the graphene-edge DEP sensing is evaluated. For instance, at each concentration, the DC response is monitored for 5 minutes to establish a baseline, and then an AC excitation is added to the gate electrode for a prescribed time (e.g., 5 minutes), and removed and the DC response monitored again. The AC voltage is centered about zero (no DC component) and the peak-to-peak value and frequency is determined based upon trapping dependent studies. In this geometry, it may be important to keep Vis much smaller than the AC peak-to-peak signal during trapping, to ensure the trapping efficiency does not change along the length of the sensors.

The second device geometry that is evaluated is the varactor geometry shown in FIGS. 2a-2c. The geometry operates in a parallel configuration and so small breaks in the graphene at the gate edges should not affect performance. The device also operates at $V_{DS}=0$, and thus does not have the problem of sensing variations at different trapping sites. The varactor configuration has the advantage that capacitance measurements are already performed at high frequencies, and thus only the amplitude of the excitation needs to be changed in order to trap DNA.

Finally, the selectivity of the sensors against interfering particles is evaluated in order to mimic the effect of sensing in realistic biological cultures. Since DNA molecules have higher electrical polarizability than proteins and lipids, it is expected that an optimal DEP frequency range and voltage can be found to concentrate DNA molecules selectively while rejecting unwanted interferants and debris.

A number of embodiments have been described. Nevertheless, it will be understood that various modifications may be made without departing from the spirit and scope of the invention. Accordingly, other embodiments are within the scope of the following claims.

What is claimed is:

1. A dielectrophoretic (DEP) sensor, comprising:
a graphene electrode adjacent a channel for confining a target particle in a liquid, the graphene electrode extending between a first electrical contact and a second electrical contact;
a surface probe attached to a surface of the graphene electrode, the surface probe having a selective reaction with the target particle;
a second electrode overlapping with the graphene electrode, the second electrode being connected to the second electrical contact;
a voltage source electrically connected to the second electrical contact and the second electrode and configured to vary a voltage between the graphene electrode and the second electrode to cause DEP trapping of the target particle at the graphene electrode; and
a source meter electrically connected to the first electrical contact and the second electrical contact and configured to apply a measurement signal to the graphene electrode, the measurement signal being sufficient to read-out a response from the DEP sensor indicative of a presence of the target particle, measure a current through the graphene electrode in response to the measurement signal, and detect the presence of the target particle at the graphene electrode based on the current.

2. The DEP sensor of claim 1, wherein the surface probe and the target particle are a complementary pair selected from the group consisting of molecules, proteins, aptamers, antibodies, lipids, vesicles, cell-derived particles, functionalized nanoparticles and whole cells.

3. The DEP sensor of claim 1, wherein the graphene electrode comprises a plurality of strips.

4. The DEP sensor of claim 3, wherein the plurality of strips are parallel to each other.

5. The DEP sensor of claim 1, wherein the DEP sensor is a resistance-based sensor.

6. The DEP sensor of claim 1, wherein the DEP sensor is a capacitance based sensor.

7. The DEP sensor of claim 1, wherein the source meter is configured to apply a DC signal as the measurement signal.

8. The DEP sensor of claim 1, wherein the source meter is configured to apply an AC signal as the measurement signal.

9. The DEP sensor of claim 1, wherein the voltage source is configured to apply an AC excitation as the voltage and the source meter is configured so that an amplitude of the measurement signal is smaller than the AC excitation.

10. The DEP sensor of claim 3, wherein each of the plurality of strips is electrically connected to a neighboring strip.

11. The DEP sensor of claim 10, wherein the plurality of strips and electrical connections form a continuous, serpentine electrode that overlaps the second electrode.

12. The DEP sensor of claim 1, wherein the second electrode comprises a plurality of parallel strips each connected at an end to a common strip, the common strip being connected to the second electrical contact.

13. The DEP sensor of claim 1, wherein the graphene electrode and the second electrode are both planar electrodes.

14. The DEP sensor of claim 13, wherein the graphene electrode and the second electrode are separated by an electrically insulating layer.

\* \* \* \* \*